(12) United States Patent
Mikkelsen et al.

(10) Patent No.: US 9,119,479 B2
(45) Date of Patent: Sep. 1, 2015

(54) ADJUSTABLE-FIRMNESS BODY SUPPORT AND METHOD

(75) Inventors: Tom D. Mikkelsen, Kingsport, TN (US); Kelly W. Chandler, Gate City, VA (US)

(73) Assignee: Tempur-Pedic Management, LLC, Lexington, KY (US)

( * ) Notice: Subject to any disclaimer, the term of this patent is extended or adjusted under 35 U.S.C. 154(b) by 591 days.

(21) Appl. No.: 13/141,558

(22) PCT Filed: Dec. 21, 2009

(86) PCT No.: PCT/US2009/069009
§ 371 (c)(1),
(2), (4) Date: Aug. 17, 2011

(87) PCT Pub. No.: WO2010/075289
PCT Pub. Date: Jul. 1, 2010

(65) Prior Publication Data
US 2011/0289683 A1   Dec. 1, 2011

Related U.S. Application Data

(60) Provisional application No. 61/139,971, filed on Dec. 22, 2008.

(51) Int. Cl.
*A47C 21/04* (2006.01)
*A47C 27/14* (2006.01)
*A47C 21/06* (2006.01)

(52) U.S. Cl.
CPC .............. *A47C 21/048* (2013.01); *A47C 21/042* (2013.01); *A47C 21/044* (2013.01); *A47C 21/06* (2013.01); *A47C 27/14* (2013.01); *A61G 2210/70* (2013.01); *A61G 2210/90* (2013.01)

(58) Field of Classification Search
CPC ................ A47C 21/042–21/048; A47C 27/14; A61G 2210/70; A61G 2210/90
USPC ....................................................... 5/421, 423
See application file for complete search history.

(56) References Cited

U.S. PATENT DOCUMENTS

| | | |
|---|---|---|
| 3,644,950 A | 2/1972 | Lindsay, Jr. |
| 4,162,393 A | 7/1979 | Balboni |
| 4,423,308 A | 12/1983 | Callaway et al. |
| 5,020,176 A | 6/1991 | Dotson |

(Continued)

OTHER PUBLICATIONS

PCT/US2009/069009 International Search Report.

*Primary Examiner* — Peter M Cuomo
*Assistant Examiner* — Brittany Wilson
(74) *Attorney, Agent, or Firm* — J. Mark Wilkinson, Esq.

(57) ABSTRACT

The present invention provides a body support assembly comprising a layer having a passage, a pump positioned to create a flow of fluid through the passage, a sensor that detects a parameter and produces a signal, and a controller coupled to the sensor and programmed to control the flow of fluid based on the signal. Preferably, the layer comprises visco-elastic foam. In one embodiment, the parameter corresponds with a firmness of the layer (e.g., a temperature of the layer). A heat exchanger can be used to alter (e.g., heat or cool) a temperature of the fluid. The present invention further provides a method of controlling a firmness of a body support comprising sensing a sensed value of a parameter (e.g., temperature) of the body support, establishing a desired value of the parameter, comparing the sensed parameter to the desired value, and adjusting the parameter.

6 Claims, 3 Drawing Sheets

(56) References Cited

U.S. PATENT DOCUMENTS

| | | |
|---|---|---|
| 5,430,900 A | 7/1995 | Kim |
| 5,669,094 A | 9/1997 | Swanson |
| 5,894,615 A | 4/1999 | Alexander |
| 6,378,948 B1 | 4/2002 | Macher et al. |
| 6,653,363 B1 | 11/2003 | Tursi, Jr. et al. |
| 6,684,433 B2 | 2/2004 | Gior et al. |
| 6,912,749 B2 | 7/2005 | Thomas et al. |
| 8,499,389 B2 * | 8/2013 | Kirchhoff ............... 5/697 |
| 2006/0069418 A1 * | 3/2006 | Schock et al. ............ 607/104 |
| 2007/0056957 A1 * | 3/2007 | Diemer et al. ............ 219/549 |
| 2011/0225739 A1 * | 9/2011 | Hanrahan ............... 5/709 |
| 2011/0252562 A1 * | 10/2011 | Mikkelsen et al. ............ 5/421 |
| 2012/0227182 A1 * | 9/2012 | Brykalski et al. ............ 5/423 |

\* cited by examiner

ADJUSTABLE-FIRMNESS BODY SUPPORT AND METHOD

CROSS-REFERENCE TO RELATED APPLICATIONS

Priority is hereby claimed to U.S. Provisional Patent App. No. 61/139,971, filed Dec. 22, 2008, the entire contents of which is herein incorporated by reference.

BACKGROUND

Visco-elastic foam is sometimes used to form mattresses and other body supports, has the ability to conform to a user's body, and can provide pressure relief for the user's body. Many types of visco-elastic foam have a glass transition temperature at least partially within the range of temperatures at which a room can be or is likely to be maintained (e.g., 10-30° C.). Therefore, for such visco-elastic foams, the temperature of the visco-elastic foam at least partially determines the firmness of the body support. As the temperature of the body support's environment increases (such as by an increase in room temperature and/or by transmission of heat to the body support from a user's body), the firmness of the body support can be reduced. Alternatively, as the temperature of the body support's environment decreases (such as by a decrease in room temperature and/or reduction in the amount of heat provided to the body support by a user), the firmness of the body support can be increased.

A particularly desirable feature for many body supports is the ability to adjust the hardness of the body support. However, the ability to control the firmness of body supports comprising visco-elastic foam has heretofore been limited. Body supports comprising visco-elastic foam having a hardness that can be adjusted by a user would be welcome additions to the art.

SUMMARY

The present invention provides a body support assembly comprising a layer (e.g., first and second layers) having a passage (e.g., between the first and second layers), a pump positioned to create a flow of fluid through the passage, a sensor that detects a parameter and produces a signal, and a controller coupled to the sensor and programmed to control the flow of fluid based on the signal. Preferably, the layer comprises visco-elastic foam. In one embodiment, the parameter corresponds with a firmness of the layer (e.g., a temperature of the layer).

If desired, the body support assembly can further include a heat exchanger for altering (e.g., heating or cooling) a temperature of the fluid. Preferably, the body support has at least two areas, and each area has a sensor and a passage through which fluid can flow, and the controller can control the fluid through each passage to separately control the parameter of the different areas. In one embodiment, the body support assembly further includes a user interface coupled to the controller and adapted to select a desired parameter of the body support assembly.

The present invention further provides a method of controlling a firmness of a body support. The method includes sensing a sensed value of a parameter (e.g., temperature) of the body support (the parameter corresponding with the firmness of the body support), establishing a desired value of the parameter, comparing the sensed parameter to the desired value, and adjusting the parameter such that the sensed value moves toward the desired value. In one embodiment, the body support assembly further includes a user interface, and establishing comprises entering a desired firmness into the user interface. Preferably, establishing further includes determining the desired value based on the desired firmness.

In another embodiment, adjusting comprises changing a temperature of the body support. For example, changing a temperature of the body support can include changing a temperature of a fluid moving through the body support.

In some embodiments, the present invention provides a body support comprising visco-elastic foam, a fluid system including a conduit in heat-transfer relationship with the visco-elastic foam, a heat exchanger in fluid communication with the conduit, and a pump operable to pump a fluid through the at least one conduit and heat exchanger to transfer heat to or from the visco-elastic foam. The body support can also include one or more sensors positioned to measure the temperature of the visco-elastic polyurethane foam in one or more locations in or on the body support, and a controller coupled to the fluid system and sensor(s) to receive the temperatures detected by the sensor(s) and to change the operation of the pump (i.e., change the pump speed and/or turn the pump on or off) and/or heat exchanger (i.e., heating or cooling the fluid passing through the heat exchanger) based upon the temperatures detected by the sensor(s). In this manner, the firmness of the body support can be adjusted in response to pumping the heated or cooled fluid through the conduit and conducting thermal energy either to or from the visco-elastic foam.

Other aspects of the present invention will become apparent by consideration of the detailed description and accompanying drawings.

Before any embodiments of the present invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. Also, terms such as "first", "second", and "third" are used herein and in the appended claims for purposes of description and are not intended to indicate or imply relative importance or significance unless otherwise specified. The term "first" does not necessarily refer to the top most layer, rather, it refers to the first of a plurality, without indicating a particular location or position.

The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

DETAILED DESCRIPTION

Figure 1:
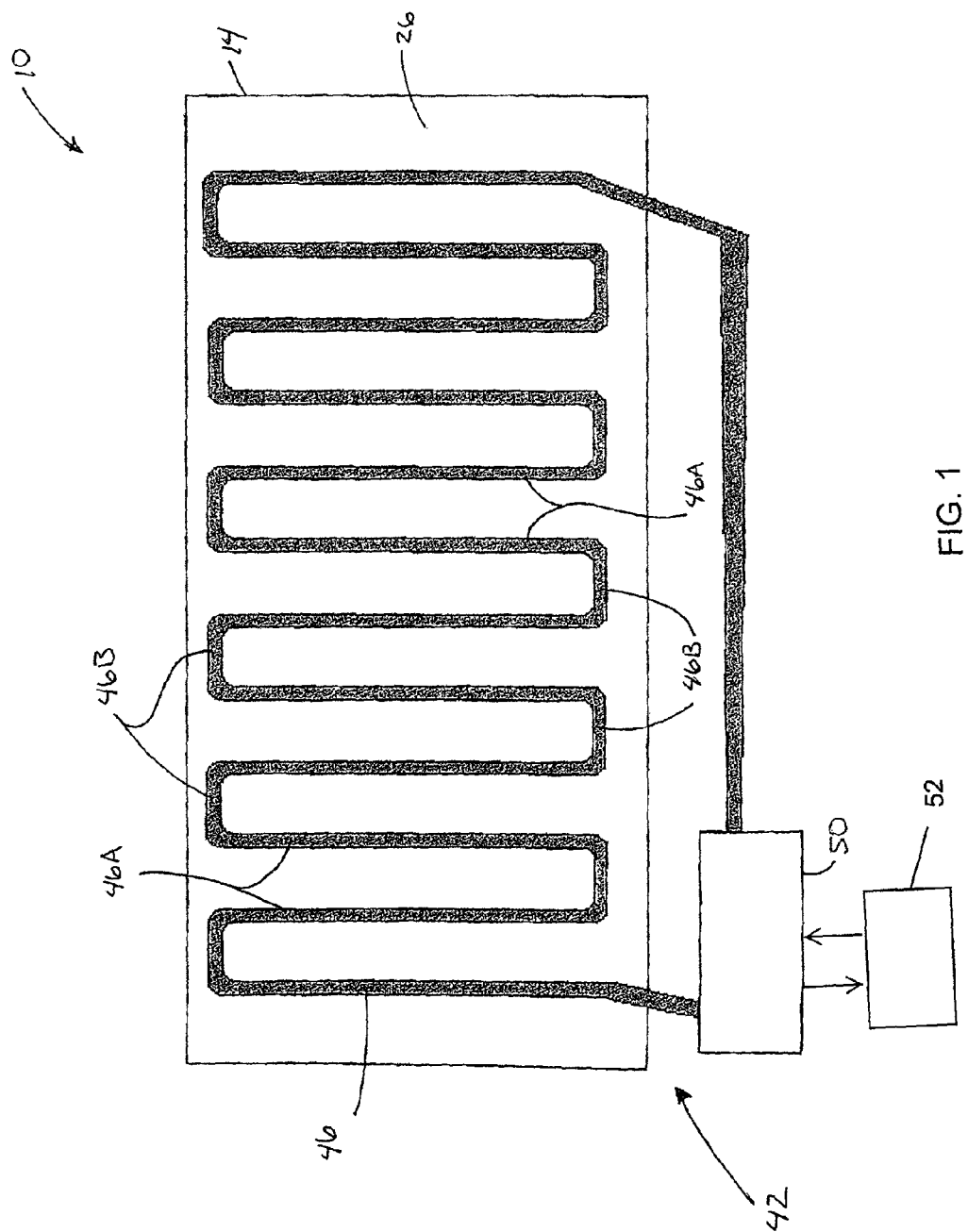
FIG. 1 is a plan sectional view of a mattress according to an embodiment of the present invention.
Figure 2:
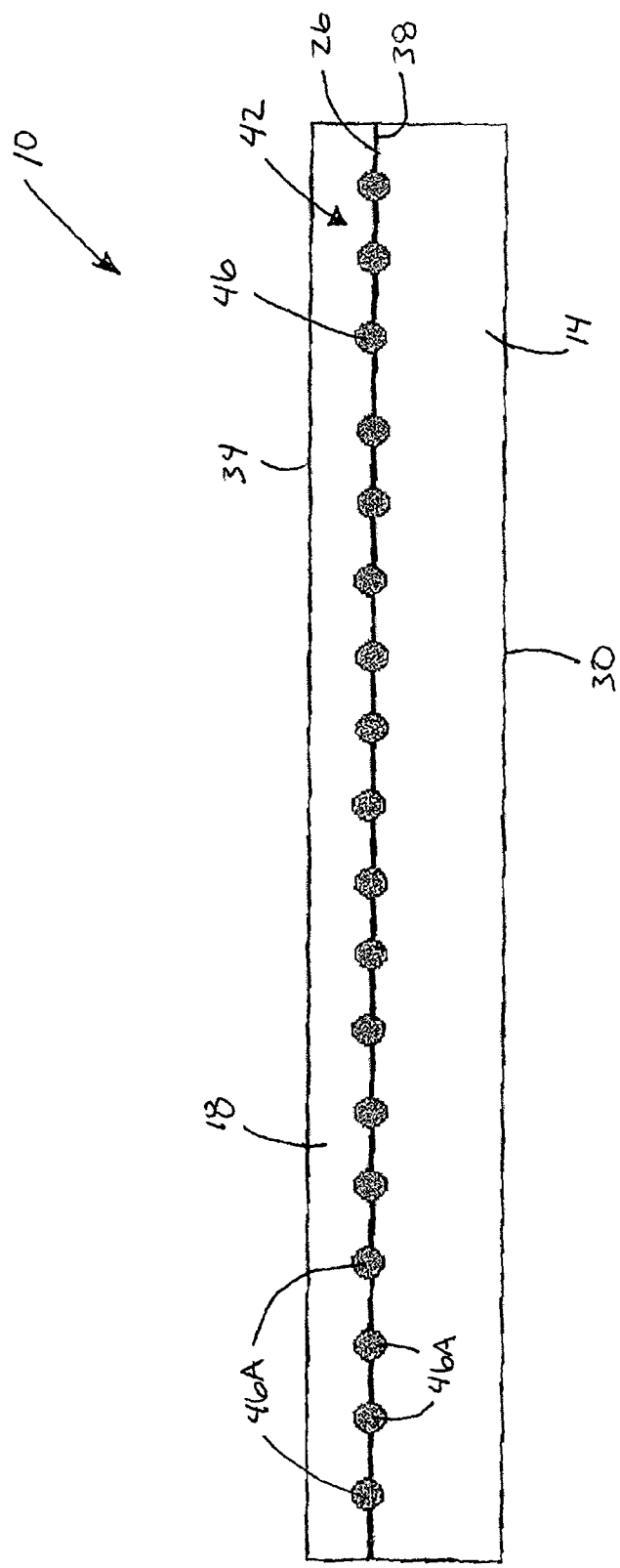
FIG. 2 is a sectional view of the mattress in FIG. 1.
Figure 3:
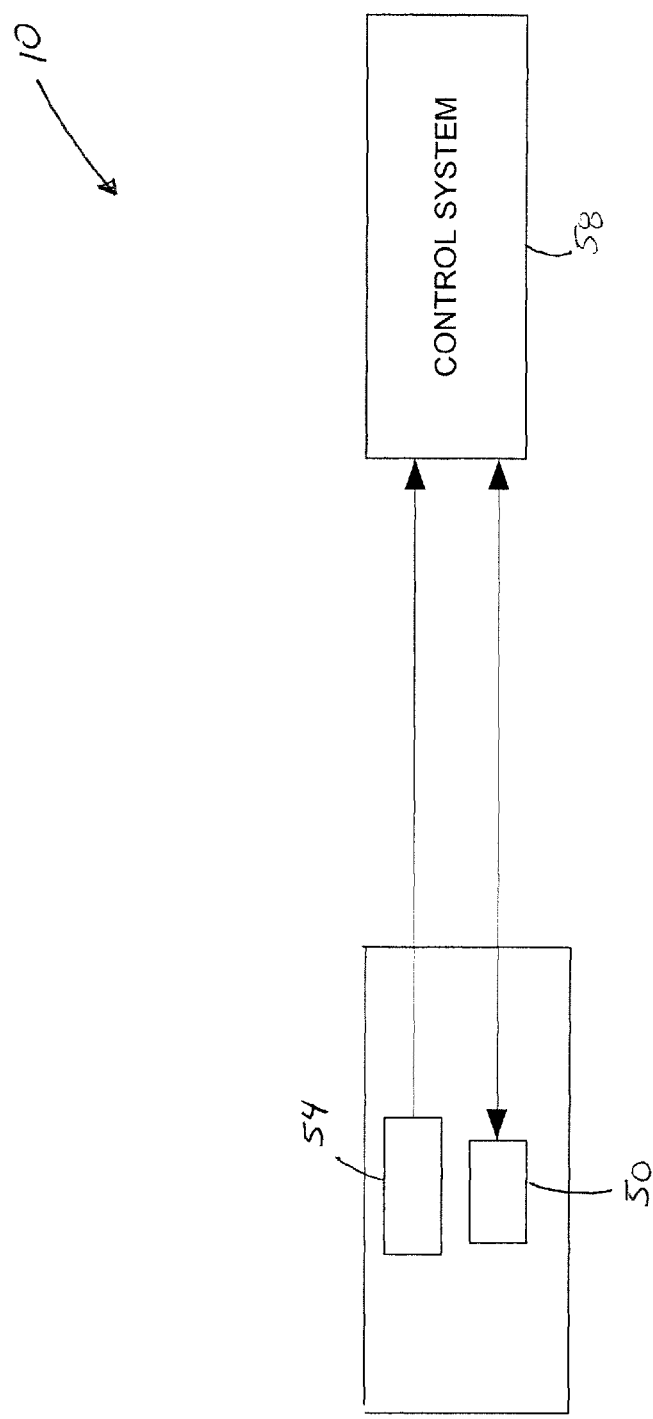
FIG. 3 is a schematic diagram of the mattress illustrated in FIG. 1, showing a controller in communication with a fluid system and a sensor of the mattress.

FIGS. 1-3 illustrate a body support 10 according to an embodiment of the present invention. In the illustrated embodiment, the body support 10 is a mattress. The illustrated body support 10 includes two layers of foam: a first layer 14 and a second layer 18 positioned above the first layer 14. In the illustrated embodiment, the first layer 14 comprises foam, such as a latex foam, reticulated or non-reticulated non-visco-elastic foam or visco-elastic foam (sometimes referred to as "memory foam" or "low resilience foam"), any polyurethane high-resilience (HR) foam, any expanded polymer (e.g., expanded ethylene vinyl acetate, polypropylene, polystyrene, or polyethylene), and the like, whereas the second layer 18 comprises reticulated or non-reticulated visco-elastic foam.

As described above, visco-elastic foam has unique low-resilience, slow-recovery, body-conforming, and pressure distributing properties that are inherently attractive for use in a wide variety of body support applications, including mattresses such as that shown in FIGS. 1-3. The visco-elastic foam described herein (e.g., whether for use in the first layer 14 or second layer 18 of the illustrated embodiment) has a hardness of at least about 20 N and no greater than about 80 N for desirable softness and body-conforming qualities. In other embodiments, the visco-elastic foam has a hardness of at least about 30 N and no greater than about 70 N for this purpose. In still other embodiments, a viscoelastic foam hardness of at least about 40 N and no greater than about 60 N is utilized. Unless otherwise specified, the hardness of a material referred to herein is measured by exerting pressure from a plate against a sample of the material to a compression of 40% of an original thickness of the material at approximately room temperature (e.g., 21-23 Degrees Celsius), wherein the 40% compression is held for a set period of time, following the International Organization of Standardization (ISO) 2439 hardness measuring standard.

The visco-elastic foam described herein can also have a density providing a relatively high degree of material durability. The density of the visco-elastic foam can also impact other characteristics of the foam, such as the manner in which the visco-elastic foam responds to pressure, and the feel of the foam. In some embodiments, the visco-elastic foam has a density of no less than about 30 kg/m$^3$ and no greater than about 150 kg/m$^3$. In other embodiments, a visco-elastic foam having a density of at least about 40 kg/m$^3$ and no greater than about 135 kg/m$^3$ is utilized. In still other embodiments, visco-elastic foam having a density of at least about 50 kg/m$^3$ and no greater than about 120 kg/m$^3$ is utilized.

The visco-elastic foam used in the various body support embodiments described and/or illustrated herein can be reticulated or non-reticulated visco-elastic foam. In this regard, reticulated visco-elastic foam has characteristics that are also well suited for use in the body support 10, including the enhanced ability to permit fluid movement through the reticulated visco-elastic foam, thereby providing enhanced air and/or heat movement within, through, and away from the reticulated visco-elastic foam. Reticulated foam (visco-elastic or otherwise) is a cellular foam structure in which the cells of the foam are essentially skeletal. In other words, the cells of the reticulated foam are each defined by a plurality of apertured windows surrounded by cell struts. The cell windows of reticulated foam can be entirely gone (leaving only the cell struts) or substantially gone. In some embodiments, the foam is considered "reticulated" if at least 50% of the windows of the cells are missing (i.e., windows having apertures therethrough, or windows that are completely missing and therefore leaving only the cell struts). Such structures can be created by destruction or other removal of cell window material, or preventing the complete formation of cell windows during the manufacturing process of the foam.

With continued reference to the illustrated embodiment of FIGS. 1-3, the second layer 18 of visco-elastic foam can be positioned above the first layer 14 without being secured thereto. However, in other embodiments, the first and second layers 14, 18 are secured to one another by adhesive or cohesive bonding material, by being bonded together during formation of the first and second layers 14, 18, by tape, hook and loop fastener material, conventional fasteners, stitches extending at least partially though the first and second layers 14, 18, or in any other suitable manner. In some embodiments, the body support 10 is constructed of fewer or more than two layers of visco-elastic foam.

With reference to FIGS. 1 and 2, each of the first and second layers 14, 18 can be substantially flat bodies having substantially planar top and bottom surfaces 26, 30, 34, 38. However, in other embodiments, one or more of the top and bottom surfaces 26, 30, 34, 38 of either or both first and second layers 14, 18 can be non-planar, including without limitation surfaces having ribs, bumps, and other protrusions of any shape and size, surfaces having grooves and other apertures that extend partially or fully through the respective layer 14, 18, and the like. Also, depending at least in part upon the application of the body support 10 (i.e., the product defined by the body support 10 or in which the body support 10 is employed), either or both of the first and second layers 14, 18 can have shapes that are not flat. By way of example only, either or both layers 14, 18 can be generally wedge-shaped, can have a concave or convex cross-sectional shape, can have a combination of convex and concave shapes, can have a stepped, faceted, or other shape, can have a complex or irregular shape, and/or can have any other shape desired.

One of the properties of visco-elastic foam is glass transition. The glass transition temperature of visco-elastic foam can impact the degree of firmness of the body support 10 (e.g., by changing the firmness of the second layer 18, and also by changing the firmness of the first layer 14 and other layers in those embodiments in which the first layer 14 and any other layers comprise visco-elastic foam). In some embodiments of the present invention, the glass transition temperature of the visco-elastic foam falls at least partially within the range of about 10° C. and about 30° C. In the illustrated embodiment, the second layer 18 changes in firmness through a range of temperatures of the second layer 18. The firmness of the body support 10 can thereby be adjusted by changing the temperature of the second layer 18. In other words, the body support 10 has a variable firmness that is controlled by the temperature of the visco-elastic foam in the second layer 18 (and in any other layer of the body support 10 comprising visco-elastic foam, in some embodiments).

As shown in FIGS. 1 and 2, the body support 10 includes a fluid system 42 utilizing a fluid to heat and/or cool the visco-elastic foam within the body support 10. The fluid system 42 can include a conduit 46 (described in greater detail below), and a pump 50 for moving fluid within the conduit 46. In some embodiments, the fluid is water. In other embodiments, fluids selected for use in the fluid system 42 include other fluids having relatively high heating and cooling capabilities, such as anti-freeze fluid, glycol, oil, and any combination thereof (whether used in conjunction with water or otherwise).

The conduit 46 extends through the body support 10 in a manner in which the conduit 46 extends across all areas of the body support 10 to enable fluid within the conduit 46 to cool or heat the visco-elastic foam within the body support 10. Any conduit shape and configuration can be used for this purpose. By way of example, the conduit shape and configuration in the illustrated embodiment is substantially serpentine, such that portions of the conduit 46A are substantially straight, extend across the body support 10, and are joined to one another at opposite ends by other portions 46B of the conduit 46 that can be bent, curved, or otherwise shaped for this purpose. The conduit 46 can be any type of hose, tube, pipe, or other structure capable of conveying fluid through the body support 10. Also, the conduit can be made of a thermally-conducting material, such as copper, stainless steel, aluminum, and other metal, thermally conductive polymer, and the like).

In some embodiments, the conduit 46 is defined by a single continuous element (e.g., pipe, tube, hose), whereas in other embodiments, the conduit 46 is defined by multiple elements connected together in any manner. Although a single serpentine run of the conduit 46 is shown in FIGS. 2 and 3, the conduit 46 can extend in a number of other manners, some of which define two or more different flow paths for fluid through the body support 10. For example, the conduit 46 can define a serpentine shape through the body support extending in a pattern oriented at 90° to that shown in FIG. 1, can define a grid within the body support 10, and the like. In any of the embodiments described and/or illustrated herein, the conduit 46 can include one or more manifolds from which multiple portions of the conduit 46 extend to define multiple discrete or non-discrete flow paths for the fluid. For example, the conduit 46 can comprise two manifolds (e.g., inlet and outlet) connected together by parallel runs of the conduit 46 extending between and fluidly connecting the manifolds in a single-pass or multiple-pass flow configuration. One or more baffles in either or both manifolds or in other locations in the conduit 46 can be used to define the number of passes the fluid must make between the manifolds.

With reference now to FIG. 2 of the illustrated embodiment, the conduit 46 of the fluid system 42 is positioned between the first and second layers 14, 18 such that the conduit 46 rests against and indents the surfaces 26, 38 of the first and second layers 14, 18, respectively. Alternatively, the facing surfaces 26, 38 of the first and/or second layers 14, 18 can be shaped to at least partially receive the conduit 46, such as by having channels shaped and dimensioned to receive the conduit 46. In either case, the first and second layers 14, 18 can cooperate to surround the cross-sectional shape of the conduit 46. In some embodiments, the conduit 46 is recessed within the second visco-elastic foam layer 18 to a greater extent than the first layer 14, or is only recessed within the second visco-elastic foam layer 18. Such a relationship between the conduit 46 and the second visco-elastic foam layer 18 can enhance the ability of the conduit 46 to heat or cool the second visco-elastic foam layer 18, thereby enhancing the ability of the conduit 46 to change the firmness of the second visco-elastic foam layer 18.

With reference now to FIGS. 1 and 3, the conduit 46 is coupled to and fluidly communicates with the pump 50 such that the conduit 46 and the pump 50 form a closed fluid circuit. In the illustrated embodiment, the pump 50 is positioned outside of the layers 14, 18 of the body support 10. However, in other embodiments, the pump 50 can be recessed within or received completely within either or both of the layers 14, 18 (e.g., received within a recess in the lower surface 30 or side surface of the first layer 14).

In the illustrated embodiment, the pump 50 is connected to a heat exchanger 52 that heats or cools the fluid moved by the pump 50 to increase and decrease, respectively, the temperature of the second layer 18. Fluid can be heated by the heat exchanger 52 in any number of manners, including without limitation by one or more electric heating elements. Alternatively, fluid can be cooled by the heat exchanger 52 by a fan directing cooling airflow past a number of heat exchanger tubes through which the fluid is moved, by Peltier cooling elements, and the like. Embodiments of the body support 10 can be capable only of heating the fluid pumped by the pump 50, capable only of cooling the fluid pumped by the pump 50, or can be capable of both heating and cooling the fluid pumped by the pump 50 (i.e., the embodiment of FIGS. 1-3).

With continued reference to FIGS. 1-3, when the temperature of the fluid is greater than the temperature of the second layer 18, thermal energy is conducted from the fluid, through the conduit 46 and to the second layer 18 to increase the temperature and decrease the firmness of the second layer 18. Similarly, when the temperature of the fluid is less than the temperature of the second layer 18, thermal energy is conducted from the second layer 18, through the conduit 46 and to the fluid to decrease the temperature and increase the firmness of the second layer 18. In other words, by increasing and decreasing the temperature of the second layer 18, the fluid system 42 decreases and increases, respectively, the degree of firmness of the body support 10.

The pump 50 can be powered by, for example, a portable power source, such as a battery (not shown), or by any other power source (e.g., household or building electric power circuit). The battery can be separate from the pump 50 and heat exchanger 52, or can be included in the same housing or frame as the pump 50 and/or heat exchanger 52. In this regard, the battery can be embedded into any portion of the body support 10, if desired.

As shown in FIG. 3, the body support 10 of the illustrated embodiment also includes a sensor 54 and a controller 58 in communication with the sensor 54. The controller 58 can be powered by the same power source as the fluid system 42 or any other power source. The controller 58 in the illustrated embodiment is also coupled to the pump 50 and heat exchanger 52. In some embodiments, a single sensor 54 is used; although in other embodiments, the body support 10 can include multiple sensors 54. The sensor(s) can be positioned on or in the body support 10 to enable measurement of the temperature (and therefore the firmness) of the visco-elastic foam of the body support 10. For example, one or more sensors 54 can be located on the top surface 34 of the second layer 18 or can be recessed within or embedded beneath the top surface 34 of the second layer 18 at any location along the length and width of the body support 10. In this manner, the sensor(s) 54 can detect the temperature of the second layer 18 at such locations, and can provide such temperature information to the controller 58. In these and other embodiments, one or more sensor(s) 54 are positioned outside of the body support 10 and instead detect the temperature of the environment around the body support 10 (thereby indirectly enabling an estimate to be made of the temperature of the second layer 18 or of any other layer of the body support 10).

As just described, the sensor(s) 54 in the illustrated embodiment are positioned to sense the temperature of the second layer 18, and can provide that information to the controller 58. In some embodiments, one or more additional sensors (not shown) can be used to sense, for example, pressure, movement, moisture, or other parameters to be provided to the controller 58. Temperature or other data can be transmitted from the sensor(s) 54 to the controller 58 via a hard-wired connection, or via a wireless connection (in which case the sensor(s) 54 can each be connected to one or more suitable transmitters, and the controller 58 can be connected to a suitable receiver for receiving the sensor data).

In some embodiments, the controller 58 is embedded into the body support 10, away from the resting position of the user's body upon the body support 10, and can share the same housing or frame as the pump 50, battery, and/or heat exchanger 52 (whether embedded within the body support 10 as described above, or otherwise). For example, the controller 58 can be located within a recess in the first layer 14, such as in a side surface of the first layer 14.

The controller 58 can be a programmable or non-programmable microprocessor capable of receiving temperature data from the sensor(s) 54 of the body support 10, processing the temperature data, and responding by changing operation of the pump 50 and/or heat exchanger 52. The controller 58 can be electrically coupled to a user interface (not shown) having one or more user-manipulatable controls, such as buttons, dials, switches, a touch screen, and the like. These controls can enable a user of the body support 10 to input desired firmness settings and/or commands to change operation of the pump 50 and/or heat exchangers 52, and in some embodiments can display body support information to the user (e.g., body support firmness, body support temperature, and the like).

The user interface can be on a housing shared with the pump 50, heat exchangers 52, and/or controller 58, or can be on another housing separate from the pump 50, heat exchangers 52, and/or controller 58. For example, the user interface can be defined on a hand-held remote in communication with the controller 58 via a wired connection (e.g., tether) or via a wireless connection (using suitable transmitters and receivers coupled to the controller 58 and user interface).

The controller 58 can receive inputs from a user via the user interface to adjust the firmness of the body support 10 (by changing the temperature of the visco-elastic foam of the body support 10). This adjustment can be made by the controller speeding or slowing operation of the pump, by stopping or starting the pump, by providing more or less electrical energy to electric heating and/or cooling elements of the heat exchanger 52, by increasing or decreasing the speed of a fan cooling the heat exchanger 52, by turning such a fan on or off, and the like (depending at least in part upon the type of heat exchanger used to heat and/or cool the fluid pumped through the body support 10).

With continued reference to the illustrated embodiment, a user can adjust or tune the temperature of the visco-elastic foam in the body support 10 to a degree that is proportional to a desired mattress firmness. In operation, the sensor(s) 54 sense the temperature of the body support 10 (e.g., the visco-elastic foam layer 18), and provides the sensed temperature to the controller 58. The controller can compare the sensed temperature to a preferred or desired temperature for the body support 10 (e.g., the second layer 18) input by the user. The controller 58 can thereafter automatically adjust the temperature of the body support 10 by controlling the pump 50, heat exchanger 52, or fan as described above until the measured temperature is the same as the desired temperature. For example, if the measured temperature is cooler than the desired temperature, then the controller 58 can increase the amount of heating (thermal) energy delivered by the heat exchanger 52 to the fluid being pumped. The heated fluid is pumped through the conduit 46, and the thermal energy in the fluid is conducted through the conduit 46 to the visco-elastic foam layer 18. As another example, if the measured temperature is warmer than the desired temperature, then the controller 58 can decrease the amount of heating (thermal) energy delivered by the heat exchanger 52 to the fluid being pumped, or can cool the fluid. The fluid is pumped through the conduit 46, and the thermal energy in the visco-elastic foam is conducted through the conduit 46 to the fluid to decrease the temperature of the visco-elastic foam layer 18.

In some embodiments, the fluid system 42 is automatically activated (i.e., the pump 50 and/or heat exchanger 52 is turned on or is placed in a state in which it can be activated by the controller 58) when a user is sensed to have rested upon the body support 10, such as by a pressure sensor as described above. Alternatively, the fluid system 42 can be activated by the user via the user interface described above. In any case, if the temperature sensed by the sensor(s) 54 indicate that the firmness of the body support is too high or too low, the controller 58 can automatically adjust the pump 50 and/or heat exchanger 52 accordingly (as also described above) to provide heat to or draw heat away from the body support 10 in order to lower or raise the firmness of the visco-elastic foam, respectively. In some embodiments, the controller 58 can be programmed to activate the fluid system 42 at a particular time of day, thereby readying the body support 10 for the user in advance of use.

In some embodiments, the controller 58 can determine when the programmed parameter (e.g., layer temperature, corresponding to layer firmness) has been reached based on data received from the sensor(s) 54. Furthermore, the controller 58 can automatically change operation of the fluid system 42 (e.g., turning the pump off, turning off the heat exchanger 52, and the like) in response to reaching the programmed, desired and/or preferred parameter.

In some embodiments, the controller 58 can regulate the temperature of one or more visco-elastic foam layers for multiple users (i.e., multiple temperature settings) and/or can regulate the temperature of one or more areas of a visco-elastic foam layer for the same user. For example, the body support 10 can be a mattress having two adjacent areas upon which two users can respectively lie. One of the two areas can be programmed to a particular firmness, while the other area can be programmed to a different firmness. In such embodiments, two different conduits 46 can extend through or otherwise be in heat exchange relationship with visco-elastic foam in the two different areas of the body support 10, and can be provided with fluid at different temperatures. In this regard, the two different conduits 46 can define separate or substantially separate closed fluid circuits, each of which operate in any of the same manners described above in connection with the embodiment of FIGS. 1-3 (i.e., with dedicated sensor(s) 54). Alternatively, the two different conduits 46 can share the same fluid, which can be independently moved through the respective conduits 46 for cooling and/or heating using the same pump 50 (with appropriate switching valve(s) in fluid communication therewith and under control of the controller 58) or using dedicated pumps 50. In any case, fluid flowing to each of the two different areas of the body support 10 can be independently heated and/or cooled using dedicated heat exchangers 52 separately controlled by the controller 58.

The features of the system described above for independently heating and/or cooling different areas of a body support 10 on which two different users lie apply equally to the control of two or more different areas of a body support 10 for the same user (e.g., head, torso, and leg areas of the body support 10). In such cases, any number of different areas of the body support 10 can have dedicated conduits 46 for moving fluid under different temperatures (i.e., heated, cooled and/or pumped independently with respect to the fluids in the other conduits 46) through the different body support areas.

In some embodiments, the fluid system 42 is removable from the body support 10. Also, in some embodiments, multiple layers of conduits 46 passing through the same or different layers of visco-elastic foam in the body support 10 can be utilized to increase and/or decrease the temperature and resulting firmness of one or more layers of visco-elastic foam at different depths of the body support 10.

In the illustrated embodiment of FIGS. 1-3, the conduit 46 of the body support 10 is located between two layers 14, 18 of the body support 10, and can be recessed within either layer 14, 18 as desired. In other embodiments, the conduit 46 can be partially or entirely embedded within a layer of the body support 10, such as entirely or partially within the viscoelastic second layer 18 of the illustrated body support 10. In such embodiments, the layer (e.g., layer 18) can be molded (e.g., injection molded, spray molded, and the like) as a single layer, with the conduit 46 embedded in the molded layer during manufacture.

The body support 10 illustrated in FIGS. 1-3 is presented in the form of a mattress. However, it will be appreciated that the features of the body support 10 described above are applicable to any other type of body support having any size and shape. By way of example only, any of the features described above are equally applicable to mattress toppers, overlays, futons, sleeper sofas, seat cushions, seat backs, and any other element used to support or cushion any part or all of a human or animal body. Accordingly, as used herein, the term "body support" is intended to refer to any and all of such elements (in addition to mattresses).

Although the invention has been described in detail with reference to certain preferred embodiments, variations and modifications exist within the scope and spirit of one or more independent aspects of the invention described.

Various features and advantages of the invention are set forth in the following claims.

What is claimed is:

1. A method of controlling a firmness of a body support comprising:

providing the body support with a conduit and a viscoelastic foam layer overlying the conduit;

sensing a sensed value of a parameter of the viscoelastic foam layer, the parameter corresponding with the firmness of the viscoelastic foam layer;

establishing a desired value of the parameter;

comparing the sensed parameter to the desired value; and adjusting the parameter such that the sensed value moves toward the desired value in response to flowing liquid through the conduit to heat or cool the overlying viscoelastic foam layer;

wherein establishing the desired value of the parameter comprises entering a desired firmness into a user interface.

2. A method as claimed in claim 1, wherein establishing the desired value of the parameter further includes determining the desired value based on the desired firmness.

3. A method as claimed in claim 1, wherein adjusting the parameter comprises changing a temperature of the viscoelastic foam layer.

4. A method as claimed in claim 3, wherein changing a temperature of the viscoelastic foam layer comprises changing a temperature of the liquid flowing through the conduit.

5. A method as claimed in claim 1, wherein the viscoelastic foam layer comprises at least two areas, and wherein the steps of sensing, establishing, comparing, and adjusting are performed separately for each area.

6. A method as claimed in claim 1, wherein the parameter comprises temperature.

\* \* \* \* \*